United States Patent [19]

Scialdone

[11] Patent Number: 6,114,493
[45] Date of Patent: Sep. 5, 2000

[54] PHOSGENATED OXIME RESINS AND THEIR PREPARATION

[75] Inventor: Mark Andrew Scialdone, Wilmington, Del.

[73] Assignee: E. I. du Pont de Nemours and Company, Wilmington, Del.

[21] Appl. No.: 09/218,634

[22] Filed: Dec. 22, 1998

Related U.S. Application Data

[63] Continuation of application No. 08/914,831, Aug. 19, 1997, Pat. No. 5,852,160.
[60] Provisional application No. 60/024,647, Aug. 22, 1996.

[51] Int. Cl.$^7$ .............................. C08G 2/00; C07C 49/00; C07C 281/00
[52] U.S. Cl. .......................... 528/220; 528/228; 528/229; 528/367; 525/471; 525/472; 525/540; 568/303; 568/305; 568/308; 568/326; 564/32; 564/35; 564/47
[58] Field of Search ..................................... 528/220, 228, 528/229, 367; 525/471, 472, 540; 568/303, 305, 308, 326; 564/32, 35, 47

[56] References Cited

U.S. PATENT DOCUMENTS

| | | | |
|---|---|---|---|
| 3,179,624 | 4/1965 | Michel | 260/63 |
| 4,085,261 | 4/1978 | Patchornik et al. | 526/19 |
| 4,180,633 | 12/1979 | Dixon | 525/359 |
| 4,413,999 | 11/1983 | Linder et al. | 8/540 |
| 5,416,193 | 5/1995 | Desai et al. | |

FOREIGN PATENT DOCUMENTS

| | | |
|---|---|---|
| 0 149 142 | 7/1985 | European Pat. Off. . |
| 15 95 645 | 8/1970 | Germany . |

OTHER PUBLICATIONS

Itoh et al., Bulletin of the Chemical Society of Japan, 50, 718–721,, 1977.
Levin et al., J. Organic Chem., vol. 37, No., 15, 1972 pp. 2455–2460.
Wicks, Prog. in Organic Coatings, 9, (1981) p3–28.
Masumi Itoh et al., Organic Syntheses, 59, 95–101,, 1975.
Nakagawa et al., J. Am. Chem. Soc., 107, 7087–7092, 1985.
DeGrado et al.,, J. Org. Chem., 45 1295–1300, 1980.

*Primary Examiner*—Samuel A. Acquah

[57] ABSTRACT

This invention relates to methods for preparing novel, solid-phase transfer reagents, specifically phosgenated oxime resins and non-symmetrical ureas, that are useful as supports in combinatorial synthesis for the creation of libraries of compounds for lead identification.

3 Claims, No Drawings

PHOSGENATED OXIME RESINS AND THEIR PREPARATION

This is a continuation of application Ser. No. 08/914,831 filed Aug. 19, 1997, now U.S. Pat. No. 5,852,160, issued Dec. 22, 1998, which claims the benefit of Provisional Application No. 60/024,647, filed Aug. 22, 1996.

FIELD OF INVENTION

The present invention relates to a method of preparation of a novel, solid-phase reagent that is useful in combinatorial synthesis for the creation of libraries of compounds for lead identification. More specifically, the method produces phosgenated oxime resins.

BACKGROUND

The facile manipulation of reactive functionality is a key factor in the development of efficient, high-yielding methods for combinatorial syntheses. For example, activated carboxylic acid derivatives have served as reactive building blocks in the solid-phase preparation of a wide variety of oligomeric and small molecule libraries. In most cases, the solid-phase protocol allows reactions on a polymer-bound scaffold to be driven to completion by making use of large excesses of reagents in solution that can be easily filtered away from the polymer support. After the scaffold has been modified, an additional cleavage step then frees the small molecule from the polymer support into solution for isolation. An alternative approach is to support a reagent or catalyst that can be used in excess to induce a chemical transformation on other reagents in solution, and once again, simple filtration can serve as a means for product separation and isolation.

Isocyanates are well known in the art to be useful intermediates in the production of pharmaceuticals and agrochemicals. A typical preparation of isocyanates involves the phosgenation of primary amines. Phosgene is a very reactive reagent, and many compounds have functional groups in addition to the primary amine which would also be react with phosgene. Therefore, many highly functionalized compounds cannot be prepared from the amine as the starting point via the isocyanate as an intermediate. Similarly, unsymmetrical ureas with different groups on each of the nitrogen atoms adjacent to the carbonyl, are also difficult to directly synthesize without the use of laboriously prepared protecting groups. A need exists to develop simple syntheses to overcome these problems.

The reaction of oximes with phosgene in solution phase to produce oxime-derived chloroformates is known in the art. Itoh et al. (Organic Syntheses, 59, 1975, 95–101 and Bull. of the Chem. Soc. of Japan, 50, 1977, 718–721) have used the reaction of various oximes with phosgene as part of a scheme to prepare a t-butoxycarbonylating reagent, which is used in peptide synthesis. The chloroformate that is formed is in the solution phase and is never isolated, but rather is used in situ. The use of the chloroformates in syntheses has the disadvantage that it must be stored and used under an inert atmosphere since they are very reactive and decompose in open air liberating HCl.

DeGrado and Kaiser (J. Org. Chem. 1980, 45, 1295–1300 and J. Org. Chem. 1982, 47, 3258–3261) have used an oxime resin as a solid phase reagent for peptide synthesis. A C-terminal amino acid is anchored onto the oxime resin as its oxime-derived ester, allowing further amino acids to be added stepwise by standard peptide coupling. Once the desired peptide is assembled, it is cleaved from the oxime resin by treatment with nucleophile such as hydrazine to afford the peptide hydrazide.

A functionalized polymer to serve as a vehicle to deliver reactive functionality, such as an isocyanate, into the solution phase, would be highly useful in the development of combinatorial syntheses for ureas, carbamates, sulfonylureas, hydantoins and other heterocyclic systems of biological importance. High yields, high recovery with few or no undesired side reactions, stability, and a suitability for automation are requirements to satisfy the need in the field.

SUMMARY OF THE INVENTION

The invention comprises the production of the novel reagent by the reaction of a source of phosgene with the polymer-bound reagent

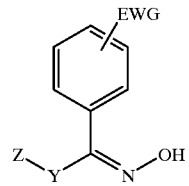

wherein Z is the recurring part of a carbonaceous polymeric backbone or sidechain thereof, Y is a pendant group of the recurring part of a carbonaceous polymeric backbone, and EWG is an electron withdrawing group. The reagent is useful as a phosgene transfer reagent in the production of isocyanates. The resulting composition is of the formula

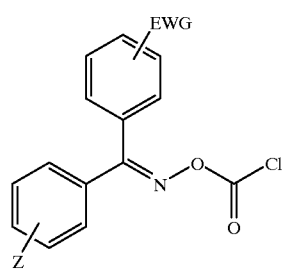

wherein Z is the recurring part of a carbonaceous polymeric backbone or side chain thereof and EWG is an electron-withdrawing group.

Additionally, the invention includes a process for preparing a solid phase reagent of the formula

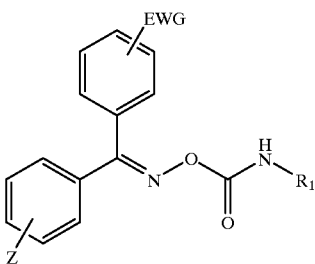

wherein Z is the recurring part of a carbonaceous polymeric backbone or side chain thereof, EWG is an electron-withdrawing group and $R_1NH$— is derived from an initial primary amine addition of the formula $R_2R_3NH$.

The invention also includes a process for preparing a non-symmetrical urea of the formula

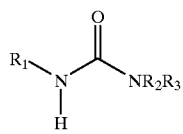

wherein $R_1$ and $R_2$ are independently selected from a group consisting of optionally substituted alkyl or optionally substituted aryl and $R_3$ is independently selected from a group consisting of optionally substituted alkyl or optionally substituted aryl or hydrogen. The non-symmetraical urea is produced by contacting the solid phase reagent of the formula

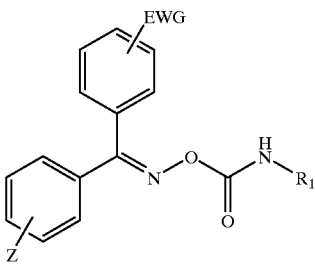

wherein Z is the recurring part of a carbonaceous polymeric backbone or side chain thereof, EWG is an electron-withdrawing group and $R_1NH$— is derived from an initial primary amine addition with an amine of the formula $R_2R_3NH$.

DETAILED DESCRIPTION OF THE INVENTION

Applicant has invented a method to prepare a novel phosgenated oxime resin. The resin is useful as a solid-phase phosgene transfer reagent to primary amines. In particular, it is useful for generating isocyanates upon thermolytic cleavage of the oxime-derived carbamate.

As used herein the following terms may be used for interpretation of the claims and specification.

scaffold—molecular framework on which functionality is presented trapping amine—amine used to trap isocyanate unsymmetrical urea—urea derived from two different amines protic input—a molecule containing a heteroatom attached to a proton The use of solid phase reagents can overcome the limitations of the prior art by serving as a vehicle to deliver reactive functionality, such as phosgene, onto desired sites of a compound. With one site, such as the isocyanate, attached to the solid-phase reagent, other sites can be manipulated at will. Cleavage from the solid support will then allow the isocyanate to be further reacted to the desired end product. The instant invention overcomes the problem of instability of the isocyanate by the immobilization of the chloroformate as part of the solid phase reagent, allowing it to be isolated, characterized and further reacted without the use of an inert atmosphere.

Since the method provides for high yields, high recovery with little or no undesired side reactions, high stability, and is suitable for automation, it is an effective tool in combinatorial synthesis.

The solid support used has the formula

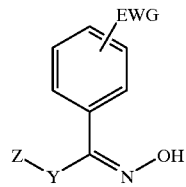

wherein Z is the recurring part of the carbonaceous polymeric backbone, Y is a pendant group of the recurring part of a carbonaceous polymeric backbone, and EWG is an electron-withdrawing group. Any polymer in which the oxime-derived carbamate functionality can be added may be used. Suitable polymers include polystyrene and polyethylene. Preferred is polystyrene, wherein Y is a pendant phenyl group of the polymer.

Any electron-withdrawing group (EWG) that is unreactive to phosgene may be used. Suitable groups include nitro, cyano, dinitro, trifluoromethyl, di-trifluoromethyl, and halogens. Preferred is a nitro group.

Phosgenation can be performed with any source of phosgene. Sources include phosgene gas and triphosgene, a commercially available solid trimer of phosgene.

The phosgenated oxime resin can be used to prepare unsymmetrical ureas where the substitutions on the nitrogens are independently selected from the group consisting of hydrogen, optionally substituted alkyl, and optionally substituted aryl. At least one of the four possible substituents on the nitrogen atoms must be hydrogen whose origin can be traced back to the primary amine used in the initial addition to the phosgenated oxime resin. In the preparation of unsymmetrical ureas, the trapping amine can be either primary optionally substituted alkyl or aryl or secondary optionally substituted alkyl.

The phosgenated oxime resin can also be used to prepare carbamates where an alcohol is used in the thermolytic cleavage trapping step instead of an amine.

The method of synthesis permits the scaffolding between the two inputs, namely the primary amine and the trapping amine in the case of unsymmetrical ureas, to be minimized. In this case, the central scaffolding of the product is essentially a carbonyl group whose origin is traced back to the phosgene. The high reactivity of phosgene is controlled by the polymer support, which may be beads, film or other form having a high surface area. This method provides a very versatile tool for the combinatorial chemist to tie protic inputs such as amines and alcohols) together on a relatively small molecular scaffolding.

One reaction path is as follows:

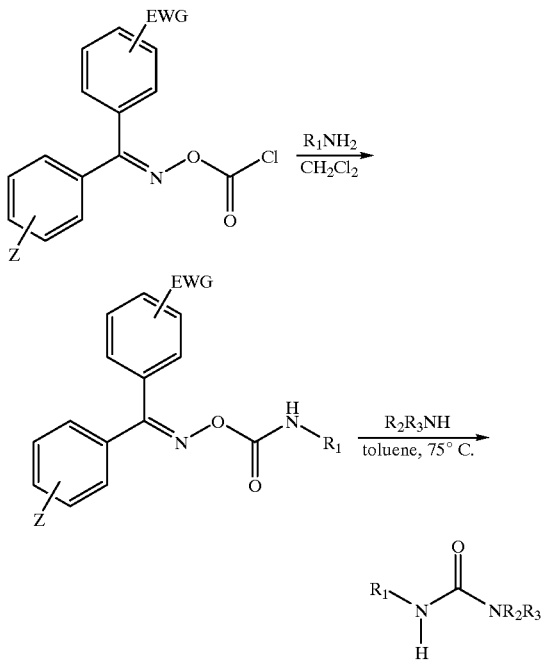

EQUIPMENT AND MATERIALS

Toluene was distilled from sodium benzophenone ketyl and dichloromethane was distilled from phosphorus pentoxide prior to use. The solid phosgene equivalent, triphosgene, was purchased from Aldrich and used directly. Amines were also purchased from Aldrich and used directly without purification. The oxime resin was prepared using Biobeads® SX-1 (1% crosslinked polystyrene) from Biorad (Hercules, Calif.). Microanalyses were carried out by Micro Analysis Inc. of Wilmington, Del. IR spectra were obtained with a Perkin-Elmer FT1600. Low resolution mass spectra were obtained with a VG Trio-2000 quadrapole mass spectrometer using the electrospray atmospheric pressure chemical ionization (APCI) technique. HPLC analyses were performed on a Hewlett-Packard 1090 liquid chromatography system using a photodiode array detector and a Zorbax SB-$C_{18}$ column.

EXAMPLES

The meaning of abbreviations is as follows: "h" means hour(s), "min" means minute(s), "sec" means second(s), and "d" means day(s).

Example 1

Preparation of Oxime Resin

The oxime resin was prepared by the method described in DeGrado, W. F.; Kaiser, E. T., J. Org. Chem. 1982, 47, 3258–3261. Before use, the resin was pre-swelled in dichloromethane (75 mL) under an atmosphere of nitrogen, then allowed to shake overnight at room temperature. 6.0 g (20 mmol) of triphosgene was weighed out in the drybox, dissolved in dichloromethane (75 mL) and added to 20 g (15 mmol, based on loading of 0.755 mmol/g resin) of the oxime resin. Filtration of the loaded resin into a solution of ethanol in dichloromethane (to quench the remaining phosgene) followed by washing with liberal amounts of dichloromethane (ca. 350 mL) and drying under vacuum overnight afforded the ketoxime chloroformate. IR (KBr) showed a strong peak at 1799 $cm^{-1}$ corresponding to the chloroformate. Cl analysis indicated the loading to be 0.663 mmol/g resin corresponding to an 88% yield.

Examples 2–9

Examples were performed following the general procedures outlined below. Substrates, products and results are given in Table 1.

1st Amine Addition

Phosgenated resin (3.0 mmol) was weighed into a 60 mL bottle. Amine ($H_2NR_1$, 9.24 mmol, 3 eq.) was weighed out and dissolved in dry dichloromethane (50 mL). Addition of the dichloromethane solution to the resin resulting in swelling of the resin and the resulting mixture was sealed and vortexed overnight at room temperature. Filtration of the resin followed by liberal washing with dichloromethane and then methanol (ca. 500 mL total) and drying under high vacuum overnight afforded urea-functionalized oxime resin. Verification of complete addition was determined by loss of the chloroformate peak and presence of the carbamate carbonyl peak between 1750 and 1760 $cm^{-1}$ in the IR spectrum. These resins were taken directly to the thermolytic cleavage without any further characterization.

Thermolytic Cleavage and Trapping Amine Addition

Primary amine-functionalized resin (0.5 mmol) was weighed into a 20 mL vial and swelled with dichloromethane until saturated (ca. 6 mL). Amine ($NHR_2R_3$, 0.55 mmol, 1.1 eq. of non-volatile amines or 2.0 mmol, 4 eq. of volatile amines) was added and the total volume was taken to 18 mL with toluene. The vial was then sealed and heated on a vortexor heating block to 75° C. overnight. The mixture was allowed to cool to room temperature and the resin was removed by filtration and washed with dichloromethane (20 mL) followed by methanol (10 mL) three consecutive times. The combined filtrates were evaporated to dryness to afford the urea product which was characterized by mass spectroscopy directly without any purification. The low resolution mass spectra were obtained with a VG Trio-2000 quadrapole mass spectrometer using the electrospray atmospheric pressure chemical ionization (APCI) technique. Yields were also determined on the unpurified product. Purity analysis was performed by HPLC on aromatic-containing urea products. HPLC analyses were performed on a Waters 2010 liquid chromatography system using a photodiode array detecotr and a Vydac C18 colum, 2.1×150 mm, starting at 100% water/0.01% TFA→100% acetonitrile/0.01% TFA. Results are indicated in Table 1.

Example 10

The reaction was performed as in the Examples above, except that a Nautlius 2400 automated synthesizer (Argonaut Technologies, Inc., San Carlos, Calif.) was used to examine the dependence of yield on cleavage temperature. The individual reactor temperature of the cleavage step was independently controlled from 50° C. to 120° C., and the yield plotted versus temperature. These results are shown in Table 2.

TABLE 1

| Example | H₂NR₁ | R₂R₃NH | Product | mw | Obs. M + 1 | Yield | Purity |
|---|---|---|---|---|---|---|---|
| 2 | 2-aminopyridine | Et₂NH | N-(pyridin-2-yl)-N',N'-diethylurea | 193.25 | 194.1 | 67% | 83% |
| 3 | 2-aminopyridine | morpholine | N-(pyridin-2-yl)morpholine-4-carboxamide | 207.23 | 208.1 | 72% | 92% |
| 4 | 2-aminopyridine | tetrahydrofurfurylamine | N-(pyridin-2-yl)-N'-(tetrahydrofuran-2-ylmethyl)urea | 221.26 | 222.2 | 72% | 79% |
| 5 | cyclohexylamine | morpholine | N-cyclohexylmorpholine-4-carboxamide | 212.29 | 213.2 | 81% | — |
| 6 | cyclohexylamine | tetrahydrofurfurylamine | N-cyclohexyl-N'-(tetrahydrofuran-2-ylmethyl)urea | 226.32 | 227.2 | 89% | — |
| 7 | benzylamine | Et₂NH | N-benzyl-N',N'-diethylurea | 206.29 | 207.2 | 92% | 93% |
| 8 | piperonylamine | Et₂NH | N-piperonyl-N',N'-diethylurea | 250.30 | 251.2 | 92% | 76% |
| 9 | N-benzyl-alaninamide | morpholine | N-benzyl-2-(morpholine-4-carboxamido)propanamide | 291.4 | 292.2 | 62% | 82% |

TABLE 1-continued

| Example | H₂NR₁ | R₂R₃NH | Product | mw | Obs. M + 1 | Yield | Purity |
|---|---|---|---|---|---|---|---|
| 10 | | | 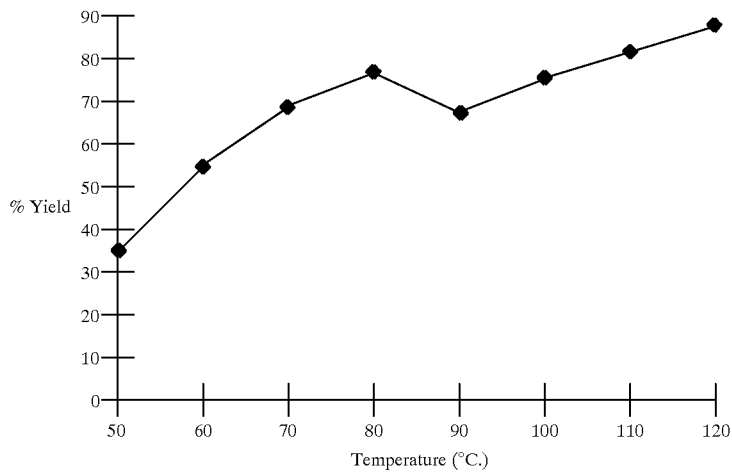 | 294.4 | 295.2 | 86% | 98% |

TABLE 2

Isolated Yield of Cyclohexyl-4-Biphenylurea as a Function of Temperature

[Graph: % Yield vs Temperature (°C), with data points rising from ~35% at 50°C to ~88% at 120°C]

I claim:

1. A method of phosgenation comprising:

contacting a compound to be phosgenated with an excess of a phosgene source in the form of a solid phase reagent of the formula

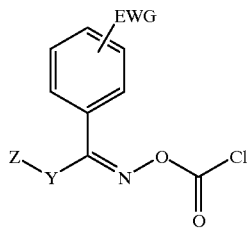

wherein Z is the recurring part of a carbonaceous polymeric backbone or side chain thereof, Y is a pendant group of the recurring part of the carbonaceous backbone, and EWG is an electron withdrawing group.

2. A method of using a solid phase reagent as a phosgene transfer reagent comprising contacting the solid phase reagent of the formula

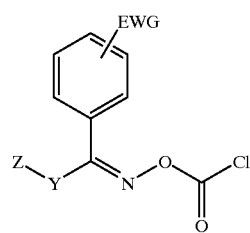

wherein Z is the recurring part of a carbonaceous polymeric backbone or side chain thereof, Y is a pendant group of the recurring part of the carbonaceous backbone, and EWG is an electron withdrawing group with a compound to be phosgenated.

3. A process for preparing a solid phase reagent useful in chemical synthesis comprising:

reacting an excess of phosgene with a ketoxime of the formula

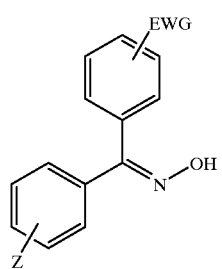
wherein Z is the recurring part of a carbonaceous polymeric backbone or side chain thereof and EWG is at least one electron-withdrawing group unreactive to phosgene, to produce the corresponding oxime-derived chloroformate.
* * * * *